(12) United States Patent
Jerome et al.

(10) Patent No.: US 7,384,584 B2
(45) Date of Patent: Jun. 10, 2008

(54) DIABETIC WALKER

(75) Inventors: Matthew D. Jerome, Altamonte Springs, FL (US); Alan T. Sandifer, Winter Springs, FL (US); Shannon R. Schwenn, Deltona, FL (US)

(73) Assignee: Orthomerica Products, Inc., Orlando, FL (US)

(*) Notice: Subject to any disclaimer, the term of this patent is extended or adjusted under 35 U.S.C. 154(b) by 302 days.

(21) Appl. No.: 11/018,730

(22) Filed: Dec. 21, 2004

(65) Prior Publication Data
US 2006/0135899 A1 Jun. 22, 2006

(51) Int. Cl.
*B29C 33/38* (2006.01)
(52) U.S. Cl. .................... 264/222; 36/44; 264/320
(58) Field of Classification Search .......... 264/220, 264/222, 223, 225, 320; 29/527.1; 36/43, 36/44
See application file for complete search history.

(56) References Cited

U.S. PATENT DOCUMENTS

| 4,414,965 | A |   | 11/1983 | Mauldin et al. |
| 4,446,856 | A |   | 5/1984 | Jordan |
| 4,478,214 | A |   | 10/1984 | Lamont |
| 4,505,269 | A |   | 3/1985 | Davies et al. |
| 4,572,169 | A |   | 2/1986 | Mauldin et al. |
| 4,639,239 | A |   | 1/1987 | Thirion de Briel et al. |
| 4,669,142 | A | * | 6/1987 | Meyer .................... 36/44 |
| 4,693,239 | A |   | 9/1987 | Clover, Jr. |
| 4,756,096 | A | * | 7/1988 | Meyer .................... 36/44 |
| 4,771,768 | A |   | 9/1988 | Crispin |
| 4,901,390 | A | * | 2/1990 | Daley ................... 12/142 N |
| 5,078,128 | A |   | 1/1992 | Grim et al. |
| 5,092,321 | A |   | 3/1992 | Spademan |
| 5,143,058 | A |   | 9/1992 | Luber et al. |
| 5,176,623 | A |   | 1/1993 | Stetman et al. |
| 5,183,036 | A |   | 2/1993 | Spademan |
| 5,197,942 | A |   | 3/1993 | Brady |
| 5,226,245 | A |   | 7/1993 | Lamont |
| 5,250,021 | A |   | 10/1993 | Chang |
| 5,329,705 | A |   | 7/1994 | Grim et al. |
| 5,329,706 | A |   | 7/1994 | Pozzobon |
| 5,368,551 | A |   | 11/1994 | Zuckerman |
| 5,370,133 | A |   | 12/1994 | Darby et al. |
| 5,399,152 | A |   | 3/1995 | Habermeyer et al. |
| 5,425,701 | A |   | 6/1995 | Oster et al. |
| 5,429,588 | A |   | 7/1995 | Young et al. |
| 5,460,600 | A |   | 10/1995 | Bieling |
| 5,491,909 | A |   | 2/1996 | Darby |
| 5,577,998 | A |   | 11/1996 | Johnson, Jr. et al. |
| 5,593,383 | A |   | 1/1997 | DeToro |
| 5,605,535 | A |   | 2/1997 | Lepage |
| 5,609,570 | A |   | 3/1997 | Lamont |
| 5,735,805 | A |   | 4/1998 | Wasserman et al. |
| 5,761,834 | A |   | 6/1998 | Grim et al. |
| 5,797,862 | A |   | 8/1998 | Lamont |
| 5,799,659 | A |   | 9/1998 | Stano |
| 5,827,210 | A |   | 10/1998 | Antar et al. |
| 5,833,639 | A |   | 11/1998 | Nunes et al. |

(Continued)

Primary Examiner—Jill L. Heitbrink

(57) ABSTRACT

A boot having a hinged shell assembly sized and dimensioned to receive a person's foot, and a customized insole. The shell assembly includes a lower shell, and an upper shell that overlaps the lower shell. The upper shell and lower shell are hinged together at or near a toe of the boot. In one instance, the upper and lower shell are hinged together by a tab that is part of the upper shell.

26 Claims, 10 Drawing Sheets

U.S. PATENT DOCUMENTS

| | | |
|---|---|---|
| 5,833,640 A | 11/1998 | Vazquez, Jr. et al. |
| 5,857,987 A | 1/1999 | Habermeyer |
| 5,876,364 A | 3/1999 | Herbst |
| 6,021,780 A | 2/2000 | Darby |
| 6,024,712 A | 2/2000 | Iglesias et al. |
| 6,083,185 A | 7/2000 | Lamont |
| 6,228,044 B1 | 5/2001 | Jensen et al. |
| 6,277,087 B1 | 8/2001 | Hess et al. |
| 6,361,514 B1 | 3/2002 | Brown et al. |
| 6,491,654 B2 | 12/2002 | Lamont |
| 6,589,194 B1 | 7/2003 | Calderon et al. |
| 6,682,497 B2 | 1/2004 | Jensen et al. |

\* cited by examiner

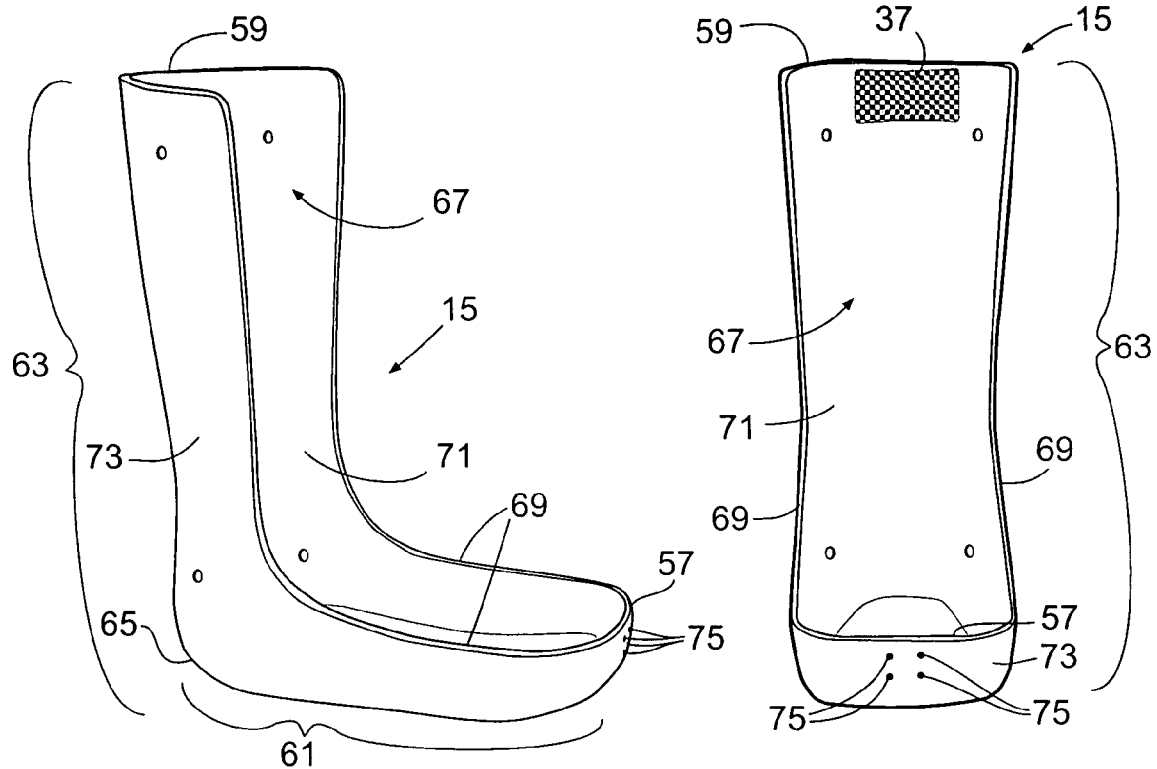
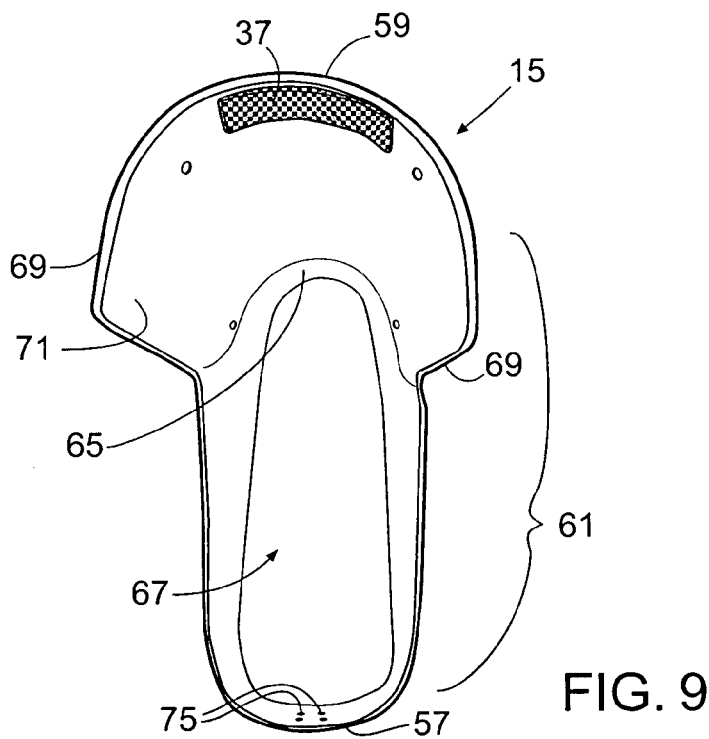
FIG. 7  FIG. 8
FIG. 9

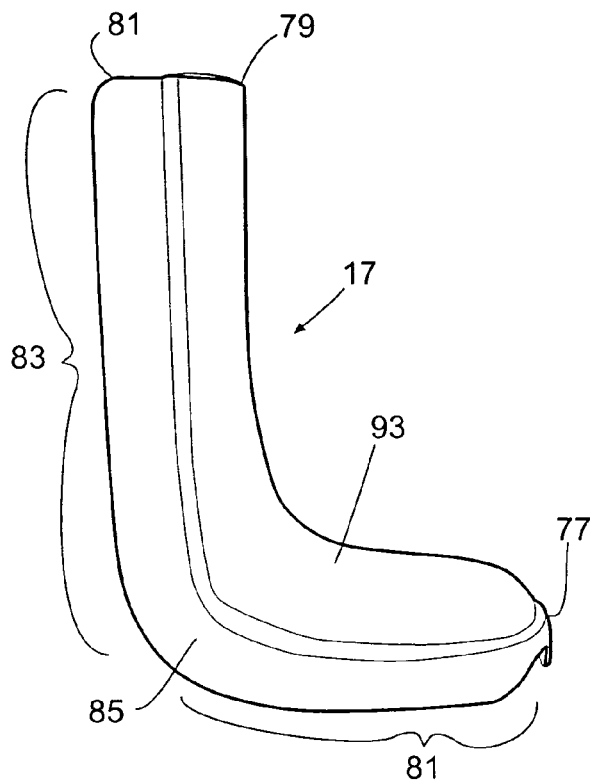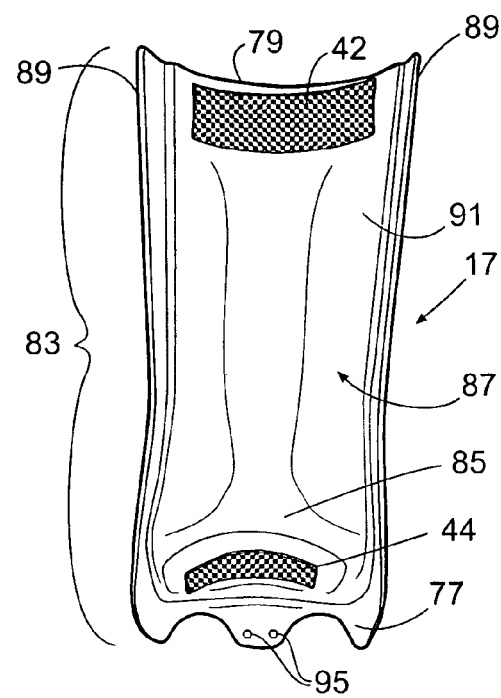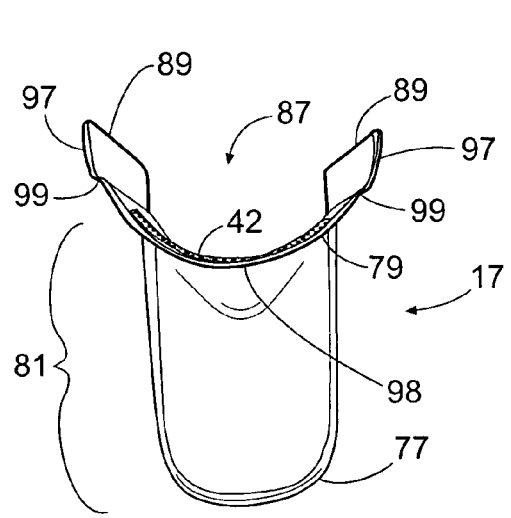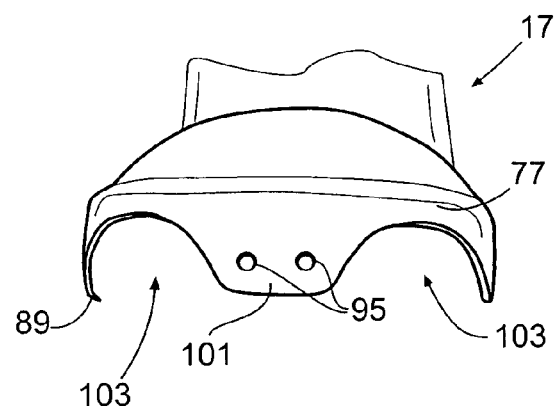
FIG. 10
FIG. 11
FIG. 12
FIG. 13

DIABETIC WALKER

FIELD OF THE INVENTION

The present invention relates generally to orthopedic boots and braces.

BACKGROUND OF THE INVENTION

Treating foot sores or ulcerations, particularly diabetic foot ulcerations, is important. Failure to properly treat such sores or ulcerations may result in amputation of the affected foot. Unfortunately, such treatment is often difficult to achieve. At least some of the problems related to such treatment, as well as some proposed solutions, are discussed in U.S. Pat. No. 6,682,497, the background of which is herein incorporated by reference.

In some instances, the use of an orthopedic boot can help facilitate healing of a foot. In order to do so, the boot should be effective in promoting healing, should be easy to use to promote use by a patient, and should be affordable to facilitate a patient's access to it. To facilitate healing, the boot should reduce the weight placed on the sole of the foot, and minimize or prevent flexing of the foot within the boot in order to minimize shearing forces on any sores or ulcerations. To promote use by a patient, the boot should be easy to put on and take off, and, to the extent that it can be adjusted, be easy to adjust.

Although attempts have been made to provide effective methods and apparatus, methods and apparatus that provide an optimum balance between healing effectiveness, usability, and affordability for every patient have yet to be achieved. As such, the present disclosure provides methods and apparatus that can help achieve such a balance for at least some patients.

SUMMARY OF THE INVENTION

An instance of an embodiment of the present invention is a boot having a hinged shell assembly sized and dimensioned to receive a person's foot, and a customized insole. The shell assembly includes a lower shell, and an upper shell that overlaps the lower shell. The upper shell and lower shell are hinged together at or near a toe of the boot.

BRIEF DESCRIPTION OF THE DRAWINGS

The exact nature of this invention, as well as the objects and advantages thereof, will become readily apparent from consideration of the following specification in conjunction with the accompanying drawings in which like reference numerals designate like parts throughout the figures thereof and wherein:

FIG. 7 is a perspective side view of a lower shell of the boot of FIG. 1.

FIG. 8 is a front view of the lower shell of FIG. 7

FIG. 9 is a top view of the lower shell of FIG. 7.

FIG. 10 is a side view of an upper shell of the boot of FIG. 1.

FIG. 11 is a rear view of the shell of FIG. 10.

FIG. 12 is a top view of the shell of FIG. 10.

FIG. 13 is a detail view of the toe of the shell of FIG. 10.

DETAILED DESCRIPTION OF THE PREFERRED EMBODIMENTS

Reference will now be made to the preferred embodiments of the invention, examples of which are illustrated in the accompanying drawings. While the invention will be described in conjunction with the preferred embodiments, it will be understood that these embodiments are not intended to limit the invention. On the contrary, the invention is intended to cover alternatives, modifications and equivalents, which may be included within the spirit and scope of the invention as defined by the appended claims. In the following detailed description, numerous specific details are set forth in order to provide a thorough understanding of the present invention. However, it will be understood by one of ordinary skill in the art that the present invention may be practiced without these specific details. In other instances, well known methods, procedures, and components have not been described in detail so as not to unnecessarily obscure the important aspects of the present invention.

Boots customized to fit a specific person can be produced without having to custom fit all of the components of the boot. More particularly, a boot having a shell assembly sized and dimensioned to receive a person's foot can be produced by: (a) pre-fabricating a plurality of shell assemblies where each shell assembly is one of a limited number of pre-selected sizes; (b) pre-fabricating a plurality of assemblies to be used with the pre-fabricated shell assemblies such as fastening assemblies, sole assemblies, and weight distribution assemblies; and (c) using some of the pre-fabricated assemblies to produce a customized boot by combining the pre-fabricated assemblies with a customized insole. A customized insole, as the term is used herein, is an insole having a cavity shaped to match at least portions of the shape of the bottom and sides of the person's foot, and sized and dimensioned to receive at least the matched portions of the person's foot. If a particular size of pre-fabricated shell is selected before the customized insole is produced, the customized insole can be customized both to fit a specific person's foot, and to fit within the selected shell assembly.

Figure 1:
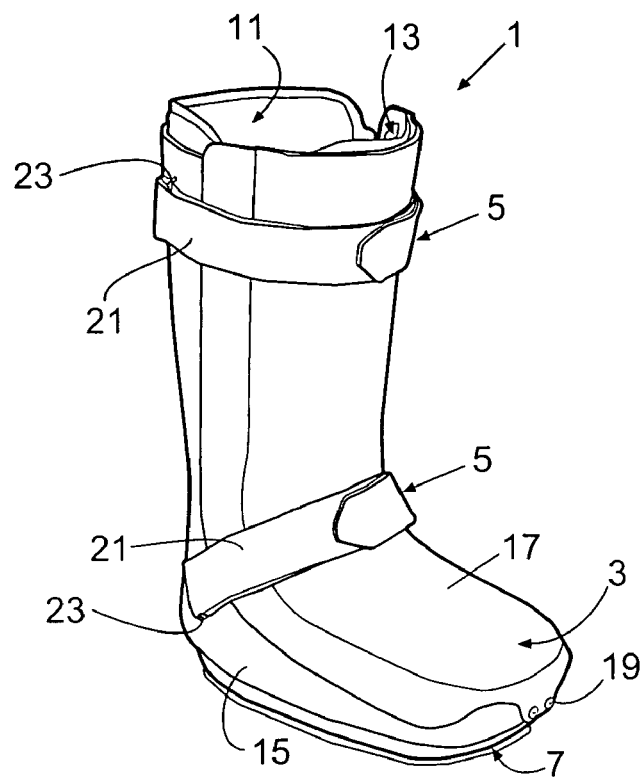
FIG. 1 is a perspective side view of an orthopedic boot in accordance with an exemplary embodiment of the invention.
Figure 2:
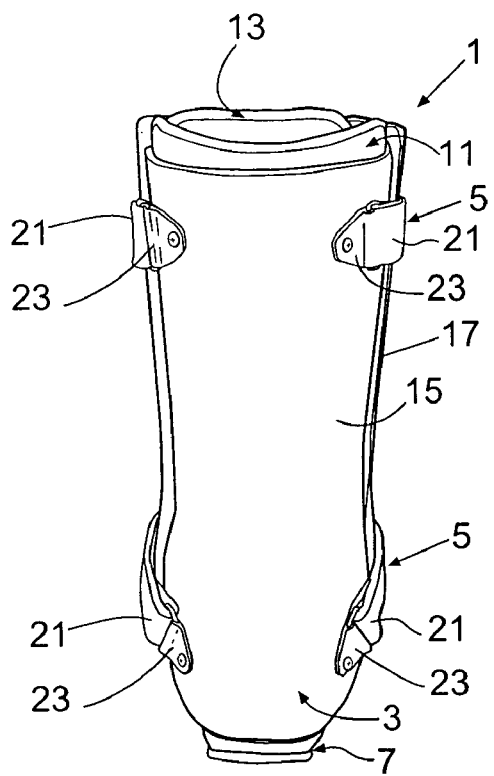
FIG. 2 is a rear view of the boot of FIG. 1.
Figure 3:
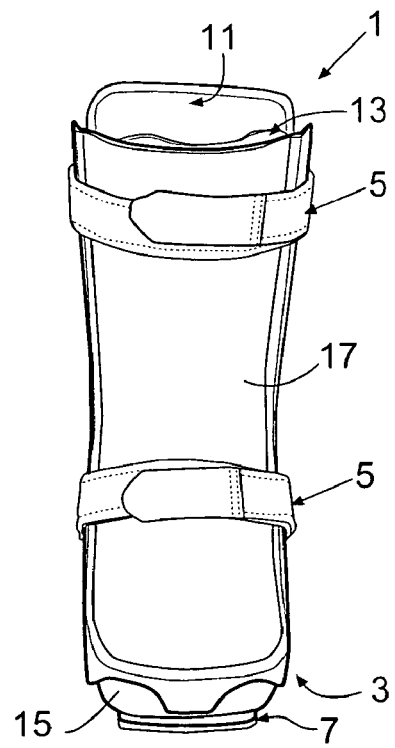
FIG. 3 is a front view of the boot of FIG. 1.
Figure 4:
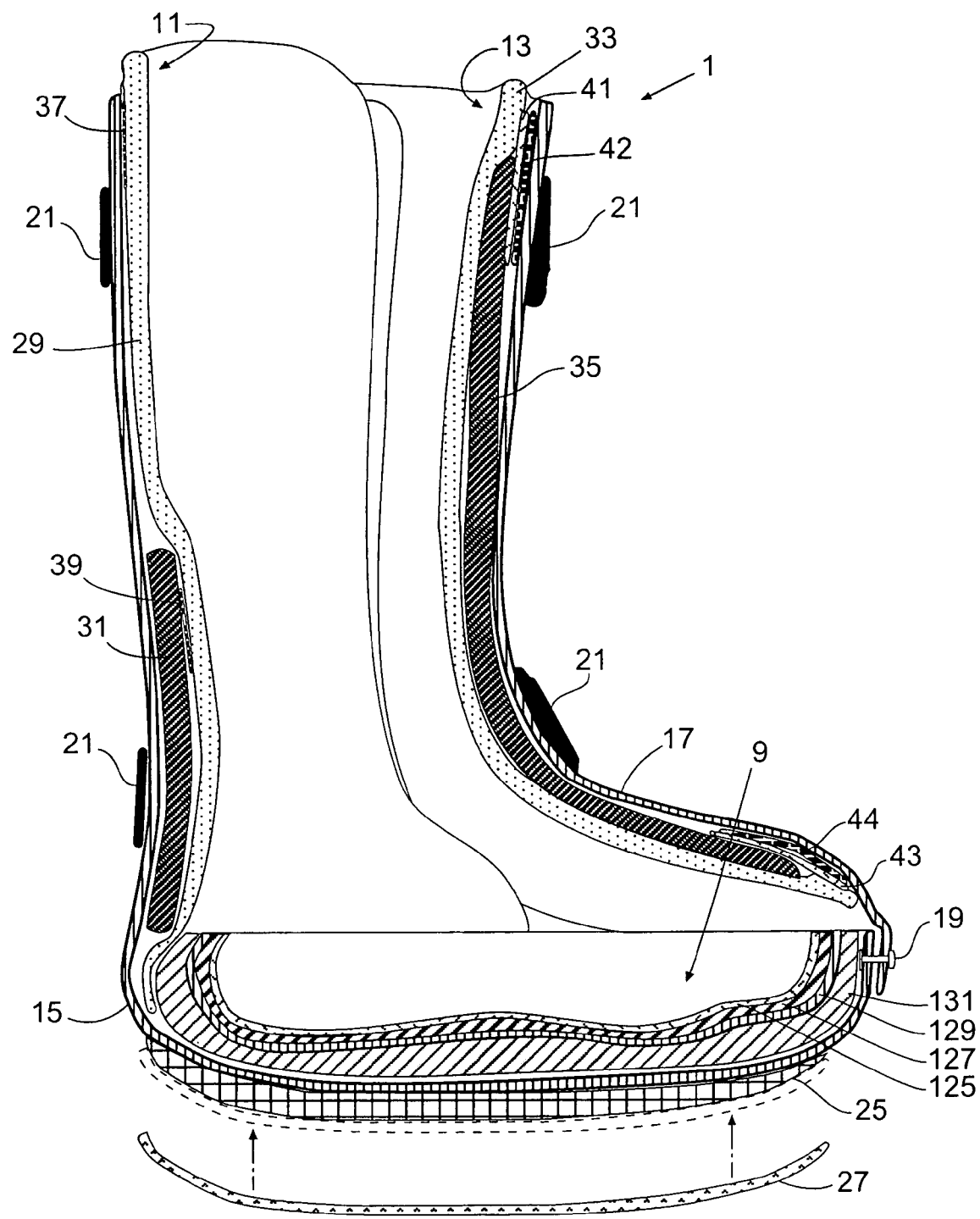
FIG. 4 is a cross sectional view of the boot of FIG. 1.

In FIG. 1, a boot 1 comprises a hinged shell assembly sized and dimensioned to receive a person's foot. As shown in FIGS. 1-4, the boot 1 comprises a hinged shell assembly 3, a fastening assembly 5, a sole assembly 7, a customized insole 9, a rear weight distribution assembly 11, and a front weight distribution assembly 13. The hinged shell assembly 3 comprises a lower shell 15, an upper shell 17, and fasteners 19. The fastening assembly 5 comprises straps 21 and swiveling strap pulleys 23. The sole assembly 7 includes a rocker 25 and a tread 27. The rear weight distribution assembly 11 comprises a rear liner 29 and an ankle pad 31. The front weight distribution assembly 13 comprises a pocketed front liner 33 and a front pad 35. The boot 1 also includes strips of hook-and-loop, i.e. Veclro®, fasteners 37, 39, 41, 42, 43, and 44. As used herein, the "shell" or "shell assembly" of the boot includes all the members that make up the external surface of the boot. The shell assembly 3 is hinged in that the lower shell 15 and the upper shell 17 are coupled together at their respective toe ends in a manner that lets the upper shell be rotated off of the lower shell to open the boot and provide easy access to the customized insole 9.

Figure 5:
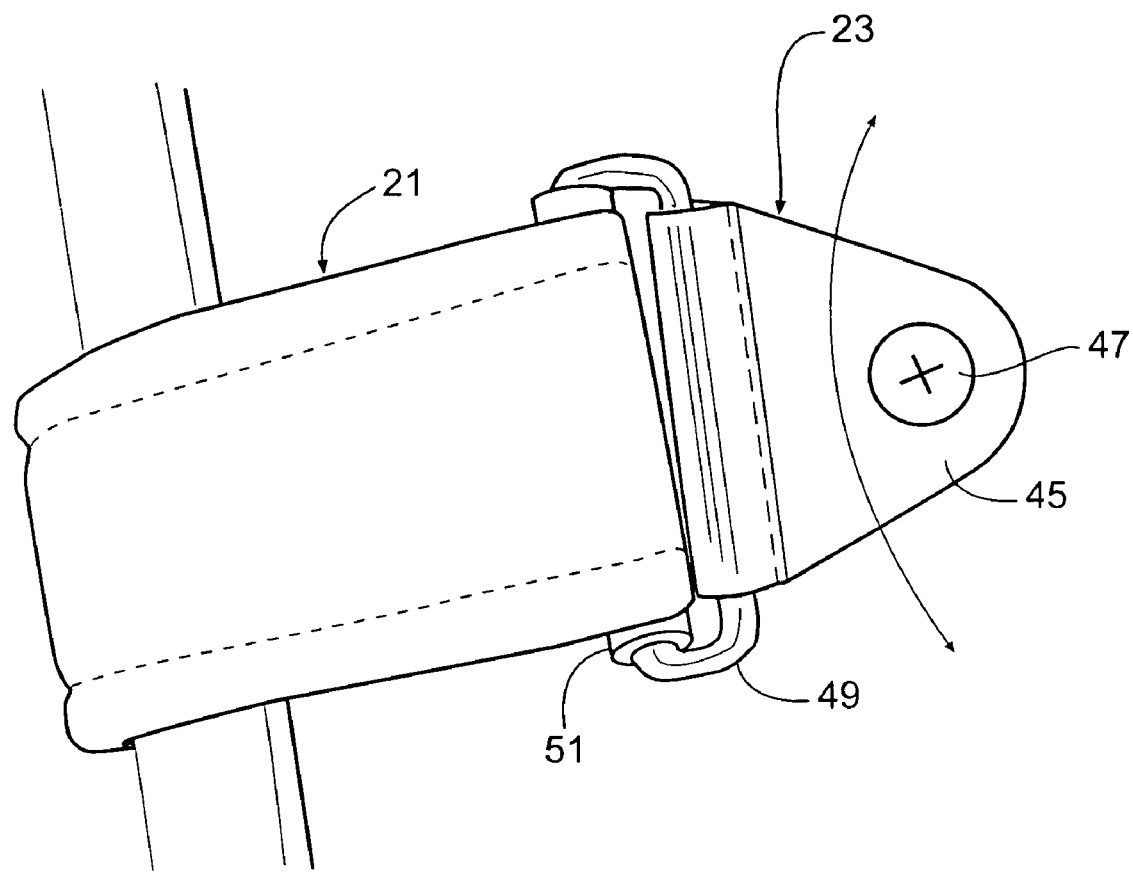
FIG. 5 is a detail view of a swiveling strap pulley of the boot of FIG. 1.

Referring to FIG. 5, the swiveling strap pulleys 23 each include a tab 45, a fastener 47, a metal loop 49, and a rotating sleeve 51. The tabs 45 and the fasteners 47 cooperate to anchor the pulleys 23 to the lower shell 15 in a manner that permits the tabs 45 to rotate around the fasteners 47. The tabs 45 provide a sleeve through which a portion of the metal loops 49 pass to couple the loops 49 to the lower shell 15. The loops 49, provide an axis around which the sleeves 51 can rotate such that the pulleys 23 can provide a mechanical advantage to a person using the straps 21 to fasten, and tighten the fit of, the boot 1. It should be noted that the pulleys 23 are found on both sides of the lower shell 15. Among other things, this permits a person to choose either the left side or the right side of lower shell 15 to anchor the straps 21 on, or to use neither side as an anchor and instead use both sides to tighten the fit of the boot 1. Additionally, the use of symmetrical anchoring assemblies like the strap pulleys 23 permits a shell assembly to be worn on either the right or left foot depending on which foot the customized insole is fitted to.

Figure 6:
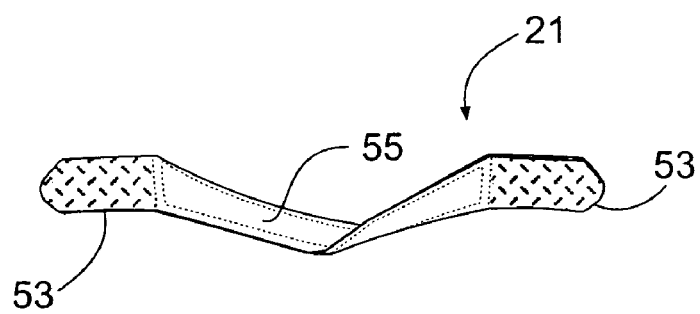
FIG. 6 is a detail view of a strap of the boot of FIG. 1.

Referring to FIG. 6, the straps 21 include ends 53, and body 55 with body 55 comprising two strips of the loop portions of hook and loop fasteners on opposite sides of the body, and the ends 53 each comprising a strip of the hook portion of a hook and loop fastener on one side. It is contemplated that having the hook strips on ends 53 positioned on opposite sides of the straps 21 may be advantageous. One possible advantage is that it allows the straps 21 to each be coupled to a strap pulley 23 such that an end 53 is positioned between the body 55 and the hinged shell assembly 3. Positioning the fastened end 53 in this manner prevents it from interfering with fastening the opposite end 53 when tightening the boot 1. With the anchored end positioned between the boot and the strap, the portion of the body 55 adjacent to the fastened end 23 is still available for fastening the opposite end 53. Alternatively, the ends 53 may have the hook strips positioned on a common side of the strap 21 to facilitate fastening and unfastening both ends of strap 21 to adjust the tightness of hinged shell assembly 3.

Although having the fastening assemblies 5 comprise the described straps 21 and the pulley assemblies 23 is advantageous, it is contemplated that alternative embodiments may utilize other types of fastening assemblies, and/or a different number of fastening assemblies. As such, a particular embodiment may utilize straps that differ from straps 21, buckles or other apparatus other than pulley assemblies 23 for coupling the straps to the upper and/or lower shells 15 and 17, or a different fastening method such as a method comprising the use of snaps and/or laces. Examples of other contemplated alternatives include small ratchet ski buckle assemblies, a compound pulley assembly consisting of a laced string through a complex of posts or pulleys providing mechanical advantage, and mechanical locking indices incorporated into the upper and lower shells.

Referring to FIGS. 7-9, the lower shell 15 of hinged shell assembly 3 comprises a toe end 57, a calf end 59, a foot segment 61, an ankle and calf segment 63, a bend 65, a cavity 67, an edge 69, an interior surface 71, an exterior surface 73, hinge fastener holes 75, and pulley assembly holes 76. Also shown in FIG. 8 is a fastening strip 37 which is used to couple the rear weight distribution assembly 11 to the lower shell 15. The lower shell 15 may be formed from plastic by molding, and may be one of a limited number of pre-determined sizes. The holes 75 are used to couple the lower shell 15 to the upper shell 17, and comprise multiple sets of holes to facilitate a choice in the positioning of the lower shell 15 and the upper shell 17 relative to each other.

Referring to FIGS. 10-13, the upper shell 17 of the hinged shell assembly 3 comprises a toe end 77, a calf end 79, a foot segment 81, an ankle and calf segment 83, a bend 85, a cavity 87, an edge 89, an interior surface 91, an exterior surface 93, hinge fastener holes 95, a flange 97, a reinforced portion 98, a shoulder 99, a tab 101, and removed portions 103. Also shown in FIGS. 11 and 12 are fastening strips 42 and 44 which are used to couple the front weight distribution assembly 13 to the upper shell 17. The upper shell 15 may be formed from plastic by molding, and may be one of a limited number of pre-determined sizes. The flange 97 is thinner than the reinforced portion 98, and includes the tab 101 formed by removing the portions 103 from the flange 97. The shoulder 99 is sized and dimensioned to match the edge 69 of the lower shell 15 such that the upper shell 17 can be positioned on the lower shell 15 by causing the flange 97 to overlap the edges 69 of the lower shell 15, and having the edges 69 abut the shoulder 99 to facilitate combining the cavities 67 and 87 to form a single cavity walled by the interior surfaces 71 and 91. The cavity thus formed will generally be large enough to receive a person's foot, as well as the customized insole 9, and the weight distribution assemblies 11 and 13. The upper shell 17 and the lower shell 15 are bolted together by the hinge fastener bolts 19 passing through the hinge fastener holes 75 and 95. The size of the cavity formed by the two shells and the relative positioning of the two shells can be adjusted by selecting a set of hinge fastening holes 75 that correspond to a desired size and/or position.

It should be noted that hinging the lower shell 15 and the upper shell 17 together allows fewer of the straps 21 to be used to couple the shells together. Coupling the tab 101 to the lower shell 15 provides all the support needed to keep the foot segments 61 and 81 of the shells 15 and 17 together. As such, the boot 1 only has two straps 21 for fastening and tightening the shell assembly 3.

It is contemplated that in some instances it may be beneficial to form the lower shell 15 and upper shell 17 as a unitary piece having a living hinge coupling the upper and lower shell portions. Such a living hinge would preferably having molecules oriented along a hinge line to improve the lifespan of the hinge. Such alignment might be achieved by flexing the hinge at least twice as the unitary piece is removed from a mold and while it is still hot. It is contemplated that it may also be beneficial to subject the hinge to a coining process so as to compresses the hinge to a pre-determined thickness, at least along a hinge line/axis.

It is contemplated that alternative embodiments may utilize other methods and/or apparatus for hinging the upper and lower shells 15 and 17 together. As such, in some instances an independent hinge assembly may be coupled to each of the upper and lower shells 15 and 17.

Although preferably formed from molded plastic, it is contemplated that the shells 15 and 17 may be formed from any other material or combination of materials that allow the shells to be formed and to function as described herein. Examples of contemplated alternatives include shells that are drape molded, blister molded, and injection molded plastics, laminated fiberglass or carbon braid with flexible resin, and shells with rigid metal or laminate superstructure frames with flexible inner boots.

Figure 14:
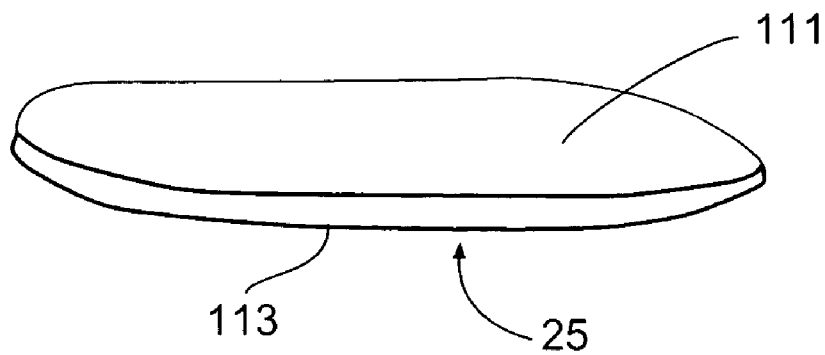
FIG. 14 is a view of a rocker of the boot of FIG. 1.

Referring to FIG. 14, the rocker 25 has an upper surface 111 shaped to conform to the bottom of the exterior surface 93 of the foot segment 61 of the lower shell 15, and a lower surface 113 that is shaped to conform to the gait of the person the boot is customized for. The rocker 25 may function to increase the rigidity of the foot segment of boot 1, to provide a cushion, and/or to provide additional stability.

Although preferably formed from ethylene vinyl acetate (EVA) foam, it is contemplated that the rocker 25 may be formed from any other material or combination of materials that allows it to be formed and to function as described herein. Examples of contemplated alternatives include urethane, rubber, and other closed cell foams matching the material characteristics of the preferred material.

Figure 15:
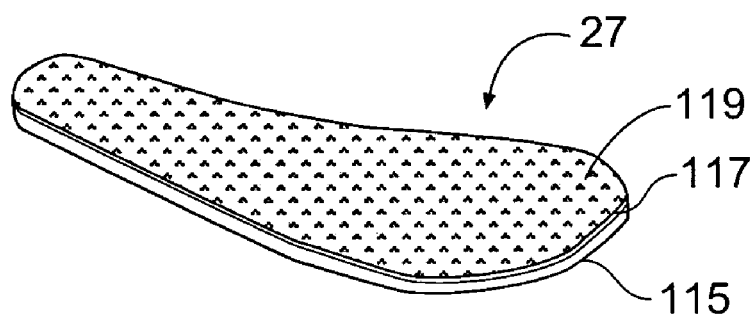
FIG. 15 is a perspective view of a tread of the boot of FIG. 1.
Figure 16:
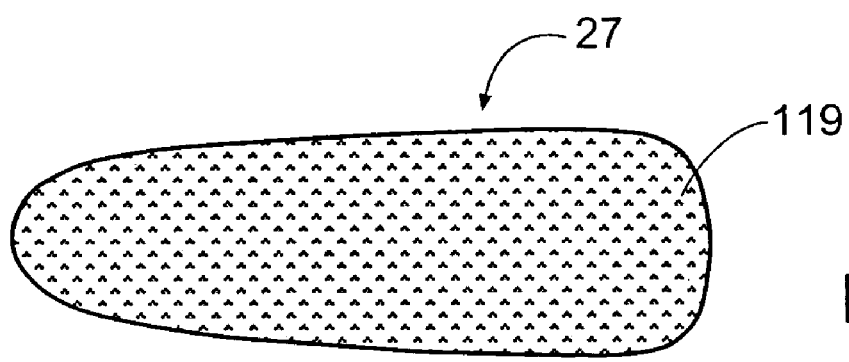
FIG. 16 is a top view of the tread of FIG. 15.
Figure 17:
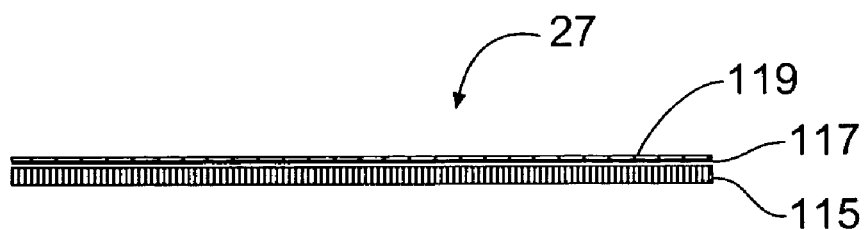
FIG. 17 is a side view of the tread of FIG. 15.

Referring to FIG. 15-17, the tread 27 comprises a layer 115 coated on one side with an adhesive layer 117 covered by a removable protective layer 119. After the rocker 25 has been shaped to customize it to a person's gait, the protective layer 119 is removed and the tread 27 is bonded to the rocker 25 by pressing the tread 27 against the rocker 25 so as to sandwich the adhesive layer 117 between the layer 115 and the layer 113. The tread 27 may function to provide the boot 1 with better traction than it would without the tread 27.

It is preferred that the tread 27 comprise a non-skid and high wear material, and that the adhesive layer 117 comprise a permanent contact cement. However, in alternative embodiments the tread 27 may comprise alternative materials and/or a different number of layers. Examples of contemplated alternatives include very high bond (VHB) adhesive tape, and single-component cyanoacrylate monomer.

Figure 18:
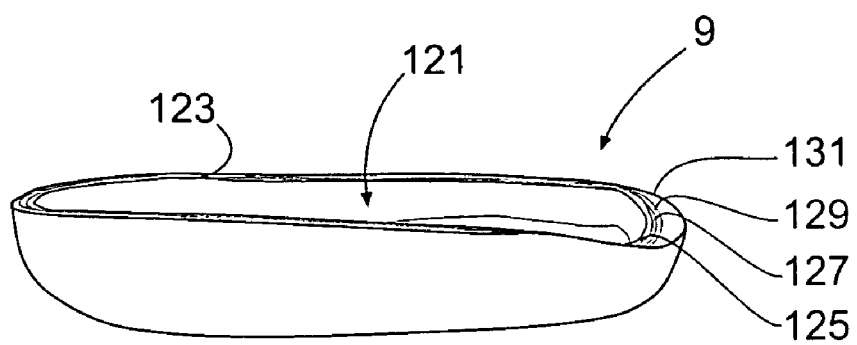
FIG. 18 is a perspective side view of a customized insole of the boot of FIG. 1.
Figure 19:
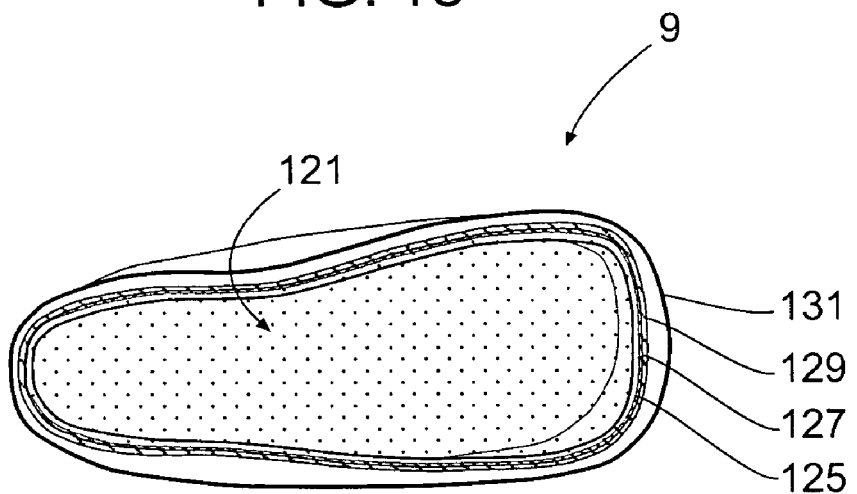
FIG. 19 is a top view of the insole of FIG. 18.
Figure 20:
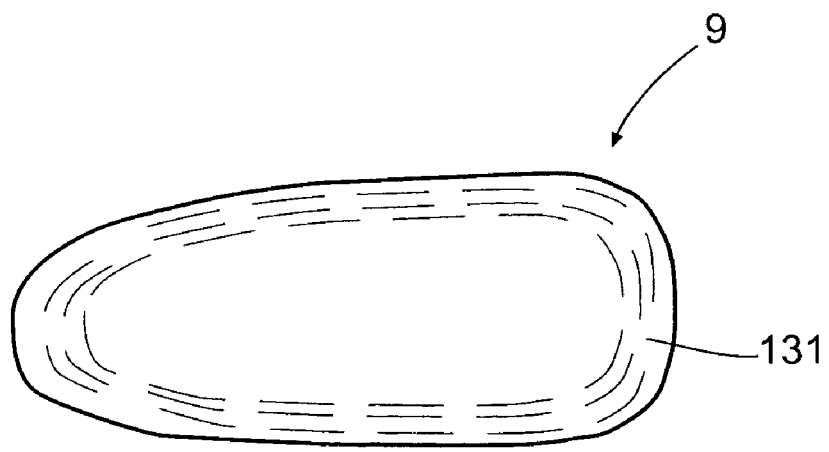
FIG. 20 is a bottom view of the insole of FIG. 18.
Figure 21:
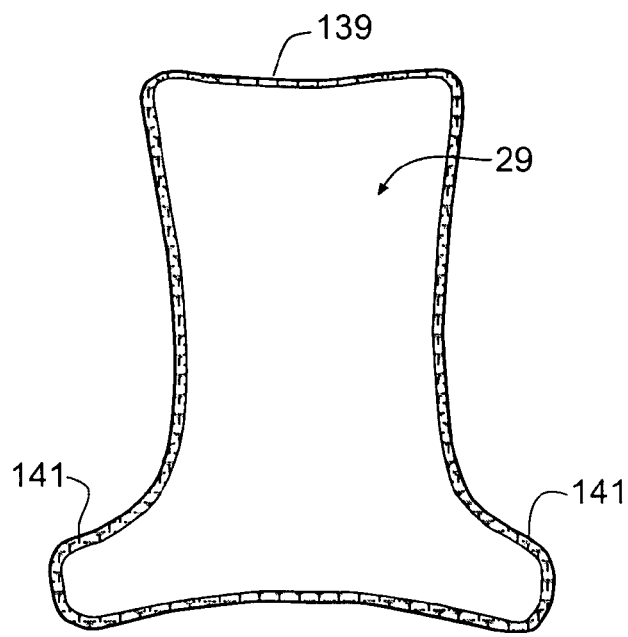
FIG. 21 is a front view of a bottom shell liner of the boot of FIG. 1.
Figure 22:
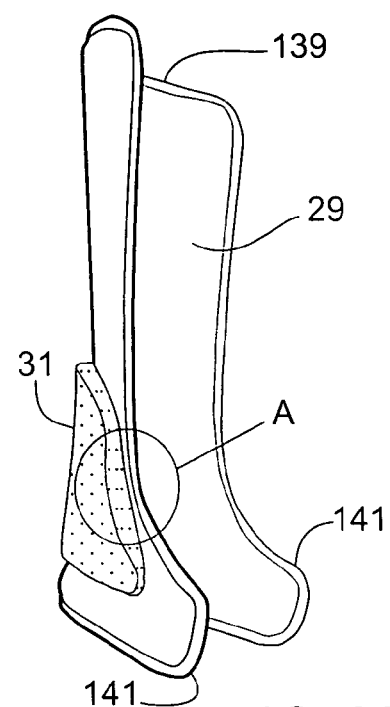
FIG. 22 is a perspective view of the liner of FIG. 21 combined with an ankle pad.
Figure 24:
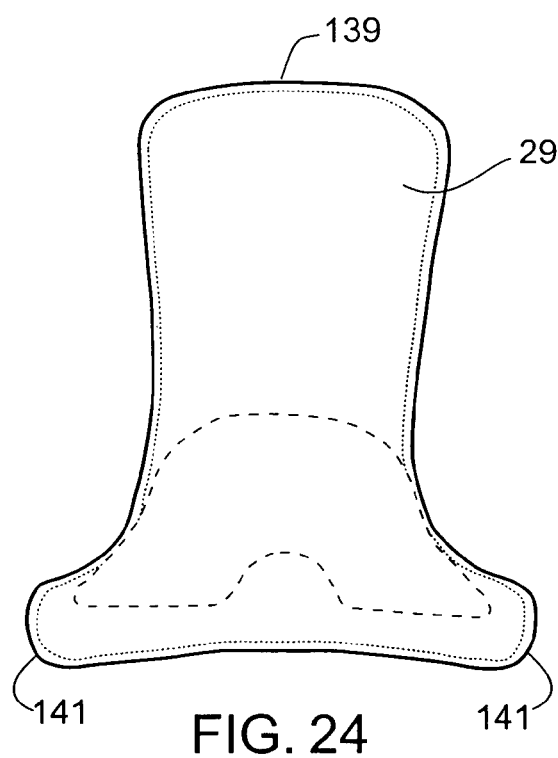
FIG. 24 is a back view of the liner of FIG. 21.
Figure 23:
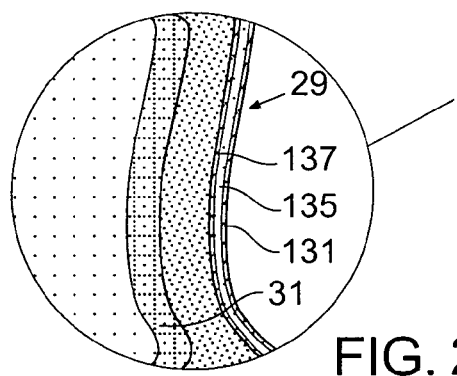
FIG. 23 is a detail cutaway view of the combination of FIG. 22.

Referring to FIGS. 18-20, the customized insole 9 has a foot receiving cavity 121 lined with a tri-laminate material 123, and a rigid bottom layer 131 of foamed plastic such as Ethafoam® polyethylene foam. The tri-laminate material 123 includes a medium density, closed cell, polyethylene foam layer 125 such as Plastazote®, a frothed, open cell urethane sheet layer 127 that is breathable, odorless, washable and non-sensitizing such as PPT/Poron®, and a higher density, closed cell, polyethylene foam layer 129 such as higher density Plastazote®. The tri-laminate material 123 provides a conforming surface for a foot received by the insole 9, while the bottom layer 131 functions to provide rigidity to the insole 9, to retain the customized shape of the cavity 121, and to provide an exterior surface that matches the shape of the interior surface 71 of the foot segment 61 of the lower shell 15. It is contemplated that matching the exterior surface of the insole 9 to the interior surface of the foot segment 61 may at least help to align a person's foot, ankle, and calf within the boot 1 to facilitate weight distribution and comfort, and to help prevent movement of the insole 9 within the lower shell 15.

The cavity 121 is sufficiently deep such that its sides extend up along the sides of a person's foot to help prevent the person's foot from sliding across the bottom of the cavity 121. It is contemplated that it would be advantageous to have the cavity 121 have a depth of at least P percent of the height of the person's foot where P is one of 10, 25, 50, 75, 90, and 100.

Figure 29:
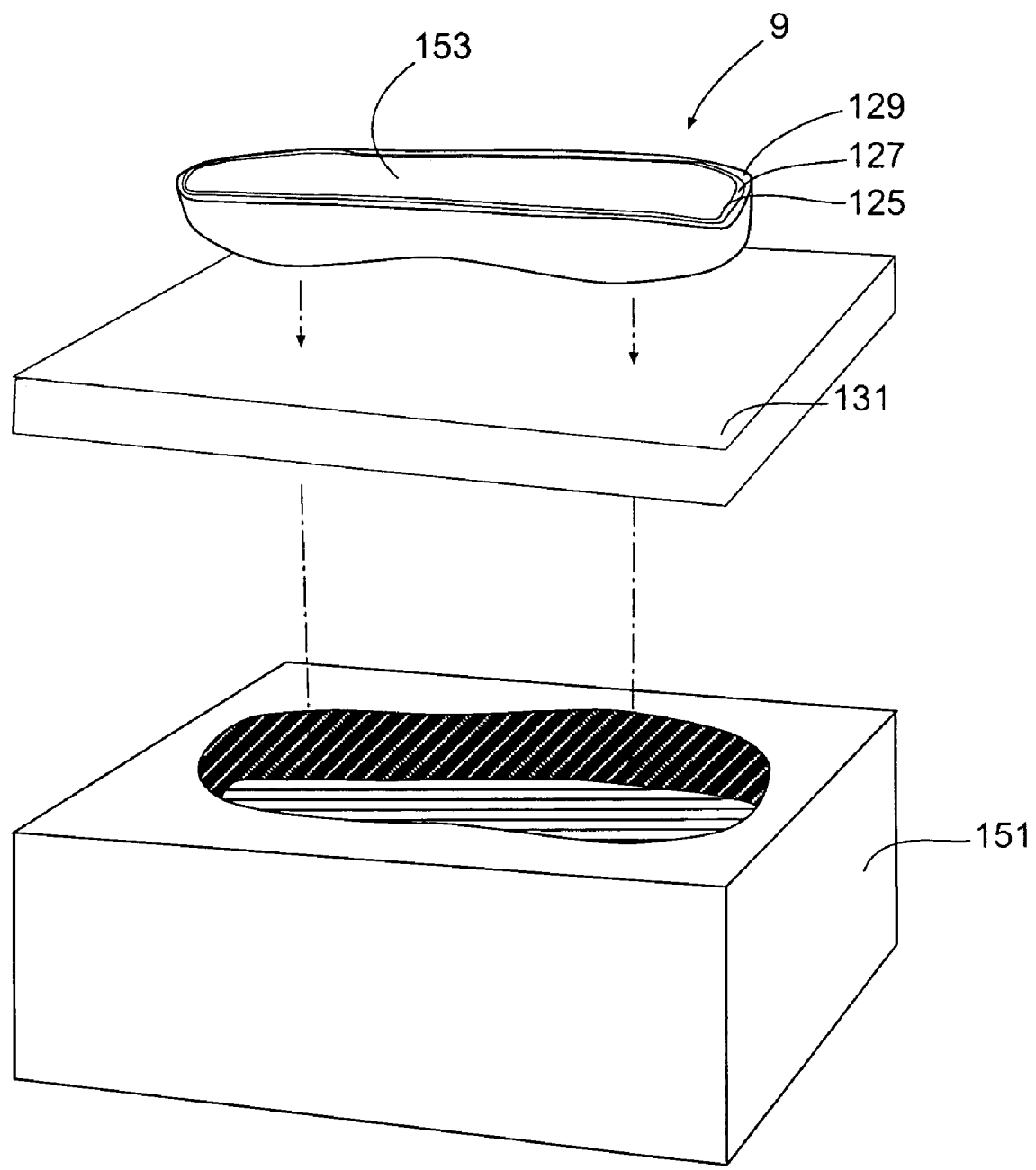
FIG. 29 is an exploded perspective view illustrating a step of a process for forming a customized insole.

The insole 9 may be formed by: (a) forming a mold of a person's foot; (b) using the mold to cast a form having a surface matching the bottom and sides of the person foot; (c) modifying the form to eliminate toe specific indentations; (d) molding the tri laminate material 123 to the form; (e) selecting a hinged boot shell assembly 3 based on the size of the person's foot, ankle and calf; (f) using the tri-laminate 123 covered form to press a deformable material (131) into a mold shaped to match a portion of the hinged boot shell (see FIG. 29); and (g) removing the insole comprising the partially covered tri-laminate 123 from the mold and removing the form from the insole. The insole 9 can then be inserted into the selected boot shell assembly 3.

Forming a mold of a person's foot may be done in any manner, but it is contemplated that it is advantageous to have the person step onto and into a block of foam material that will conform to the external shape of the person's foot and retain that shape once the person's foot is removed. Using the mold to cast a form may also be done in any manner, but it is contemplated that it is advantageous to pour plaster or some other liquid into the mold. Modifying the form to eliminate toe specific indentations may include filling indentations and/or sanding or otherwise removing portions of the cast form. Molding the tri-laminate material around the form may comprise loosely fitting a layer of tri-laminate material around the form and then forcing the material tight against the form while heating the material. It is contemplated that forming the insole 9 may also comprise the use of a two part liquid urethane foam.

Although it is preferred that the customized insole 9 comprise the described materials, it is contemplated that alternative embodiments may comprise alternative materials and/or a different number of layers. Alternative embodiments may also comprise a customized insole formed using a method entirely different from the method described herein, or that differs from the method described herein, possibly in regard to having additional or fewer steps. Examples of contemplated alternatives include the use of low temperature polyethylene foam molded directly to the patient.

Figure 25:
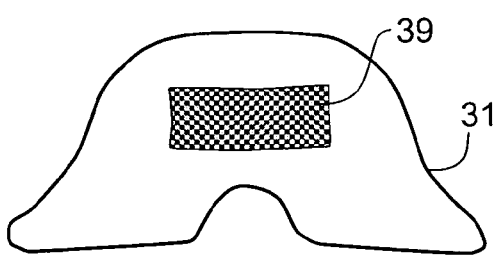
FIG. 25 is a front view of the ankle pad of FIG. 22.

Referring to FIGS. 21-25, the rear weight distribution assembly 11 comprises a rear liner 29 and an ankle pad 31. The liner 29 preferably includes cloth layers 131 and 137 enclosing a foam pad 135. FIG. 25 also shows a hook-and-loop fastening strip 39 which is used to couple the ankle pad 31 to the liner 29. The liner 29 is sized to wrap partially around the calf, ankle, and upper foot of a person wearing the boot 1, and includes a central portion 139, and wings 141. The cloth layers 131 and 137 are preferably formed from a material that can act as the loop portion of a hook-and-loop fastener such that the hook strips 37 and 39 can be coupled to the layers 131 to fasten the pad 31 to the liner 29, and the liner 29 to the lower shell 15. The broken line of FIG. 24 indicates the position of the pad 31 relative to the liner 29. As with the liner 29, the pad 31 has a central portion and wings, but the central portion is shorter such that the pad 31 does not extend much, if at all, above the ankle of a person wearing the boot 1. The pad 31 includes a central notch 32 on its bottom edge to minimize pressure on the Achilles tendon.

Figure 26:
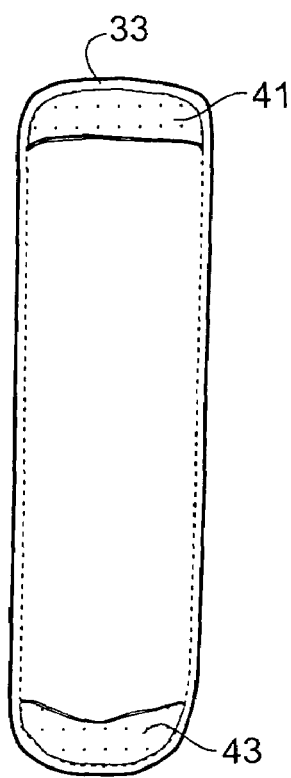
FIG. 26 is a front view of an upper shell liner of the boot of FIG. 1.
Figure 27:
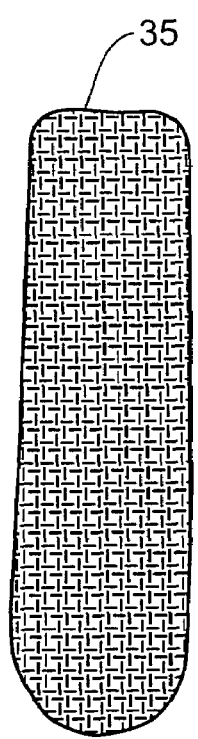
FIG. 27 is a front view of an upper shell pad of the boot of FIG. 1.
Figure 28:
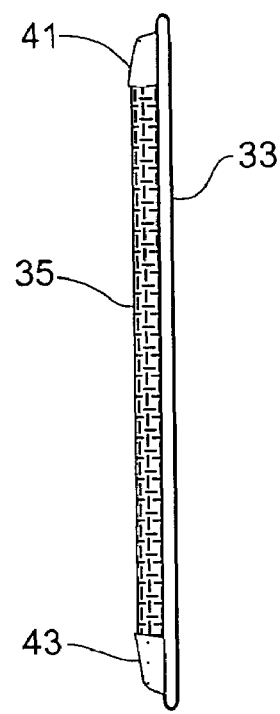
FIG. 28 is a side view of the pad of FIG. 27 combined with the liner of FIG. 26.

Referring to FIGS. 26-28, the front weight distribution assembly 13 comprises a pocketed front liner 33 and a front pad 35. The pocketed front liner 33 is preferably formed in the same fashion as the liner 29, and is sized and shaped to wrap partially around the calf, ankle, and upper foot of a person wearing boot 1, and to line the interior surface 91 of the cavity 87 of the upper shell 17. The liner 33 includes two pockets formed by loop strips 41 and 43. The pad 35 can be coupled to the liner 33 by placing the ends of the pad 35 in the pockets formed by the strips 41 and 43. Once the liner and pad are coupled together, the loop strips 41 and 43 are pressed against the hook strips 42 and 44 to couple the liner 33 and the pad 35 to the upper shell assembly 17.

The foam centers of liners 29 and 33 are made from open-cell polyester or polyether foam such as Coolfoal™. The pads 31 and 35 are made from viscoelastic foam such as polyvinyl chloride, and preferably provide equal pressure to compressing surfaces over a wide range of compression. As an example, it would likely be advantageous to utilize a material that provided substantially equal pressure whether compressed 10% or compressed 90%.

It is contemplated that alternative embodiments may utilize weight distribution assemblies in addition to those described herein, may not include a weight distribution assembly described herein, and/or may include a different type of weight distribution assembly. An examples of a contemplated alternative is the use of polyurethane foam.

The embodiments of the present invention described herein comprise multiple novel features with each described embodiment including either a single such feature or a combination of such features. Other contemplated embodiments include all combinations of one or more such novel features not explicitly described herein as such combinations are readily discernable from the embodiments described. In light of the various contemplated embodiments, the present invention can be characterized in a number of ways with the following paragraphs providing examples of some such characterizations.

It is contemplated that an instance of an embodiment of the present invention may be characterized as a boot comprising a customized insole and a hinged shell assembly forming a cavity sized and dimensioned to receive a person's foot, wherein: the assembly comprises a lower shell, and an upper shell that overlaps the lower shell; and the upper shell and lower shell are hinged together at or near a toe of the boot.

In the preceding or other instances, the boot may also be characterized as including and/or satisfying one or more of the following elements and/or recitations: (a) the upper shell and lower shell are hinged together by using a portion of the upper shell to fasten the upper shell and lower shell together; (b) the upper shell comprises an edge shaped to define a toe tab having a width less than X % of a width of the boot where X is one of 20, 30, 50, and 75, and the tab is fastened to the lower shell; (c) the position of the toe tab relative to the lower shell can be adjusted to modify the size of a cavity formed by the upper and lower shells and to change how much the upper shell overlaps the lower shell; (d) the flanged edge comprises the tab and the tab is bordered by narrowed segments of the flanged edge where the flange is narrower than it is at the tab and at other segments of the flanged edge bordering the narrowed segments; (f) the upper shell comprises a flanged edge that forms a shoulder against which an edge of the lower shell can be positioned; and (g) the shoulder is sized and dimensioned to correspond to the thickness and shape of the edge of the lower shell.

In the preceding or other instances, the boot may also be characterized as including and/or satisfying one or more of the following elements and/or recitations: (a) the boot has a customized insole, the insole having a foot receiving cavity having edges shaped to substantially conform to the perimeter of a particular person's foot and a bottom shaped to substantially conform to the bottom of the person's foot; (b) the foot receiving cavity includes one or more recesses positioned to be adjacent to one or more sores or ulcers on the person's foot; (c) the insole has an external surface comprising the bottom and sides of the insole where the surface is sized and dimensioned to match the shape of the bottom and lower portions of the sides of the lower shell; and (d) the customized insole comprises a tri-laminate material having a medium density closed cell polyethylene layer, a urethane layer, and a higher density closed cell polyethylene layer forming the foot receiving cavity, and a layer of polyethylene foam forming the external surface of the insole.

In the preceding or other instances, the boot may also be characterized as including and/or satisfying one or more of the following elements and/or recitations: (a) the boot has only two straps for holding the upper shell and lower shell together while the boot is being worn; (b) both straps are positioned to overlay the upper shell at or above a bend in the shell where the shell transitions between an ankle and/or calf segment and a foot segment; (c) the boot comprises a first removable liner coupled to the lower shell, and a second removable liner coupled to the upper shell; (d) each liner comprises a cloth exterior enclosing a foam pad; (e) the foam pad comprises open-cell polyester or polyether foam and has a thickness of less than 0.25 inches; (f) the boot further comprises a first viscoelastic pad positioned above the insole and between the first removable liner and the lower shell, and a second viscoelastic pad extending along the length of the second removable liner and positioned between the second removable liner and the upper shell; (g) the first viscoelastic pad is coupled to the first removable liner by a hook-and-loop fastener, the second viscoelastic pad extends into pockets positioned at the ends of the second removable liner, the first liner is coupled to the bottom shell by a hook-and-loop fastener positioned near an upper end of the lower shell, the first removable liner has a lower end sandwiched between the insole and the lower shell, and the second removable liner is coupled to the upper shell by hook-and-loop fasteners coupled to the pockets holding the second viscoelastic pad; and (h) the boot further comprises a rocker shaped to conform to the person's stride, and having a lower textured surface adhesively bonded to the rocker.

In the preceding or other instances, the boot may also be characterized as having a customized insole, the insole having a foot receiving cavity having edges shaped to substantially conform to the perimeter of a particular person's foot and a bottom shaped to substantially conform to the bottom of the person's foot, wherein: the foot receiving cavity includes one or more recesses positioned to be adjacent to one or more sores or ulcers on the person's foot; the insole has an external surface comprising the bottom and sides of the insole where the surface is sized and dimensioned to match the shape of the bottom and lower portions of the sides of the lower shell; and the customized insole comprises a tri-laminate material having a medium density closed cell polyethylene layer, a urethane layer, and a higher density closed cell polyethylene layer forming the inner cavity, and a layer of polyethylene foam forming the lower external surface of the insole.

In the preceding or other instances, the boot may also be characterized as having only two straps for holding the upper shell and lower shell together while the boot is being worn, and both straps are positioned to overlay the upper shell at or above a bend in the shell where the shell transitions between an ankle and/or calf segment and a foot segment.

In the preceding or other instances, the boot may also be characterized as: (a) comprising a first removable liner coupled to the lower shell, and a second removable liner coupled to the upper shell; (b) having each liner comprise a cloth exterior enclosing a foam pad comprising open-cell polyester or polyether foam and having a thickness of less than 0.25 inches; (c) comprising a first viscoelastic pad positioned above the insole and between the first removable liner and the lower shell, and a second viscoelastic pad extending along the length of the second removable liner and positioned between the second removable liner and the upper shell; and (d) the first viscoelastic pad is coupled to the first removable liner by a hook-and-loop fastener, the second viscoelastic pad extends into pockets positioned at the ends of the second removable liner, the first liner is coupled to the bottom shell by a hook-and-loop fastener positioned near an upper end of the lower shell, the first removable liner has a lower end sandwiched between the insole and the lower shell, and the second removable liner is coupled to the upper shell by hook-and-loop fasteners coupled to the pockets holding the second viscoelastic pad.

In the preceding or other instances, the boot may also be characterized as having an insole customized to a foot of a person wherein the boot is produced by: forming a mold of the person's foot; using the mold to cast a form having a surface matching the bottom and sides of the person foot; modifying the form to eliminate toe specific indentations; molding a tri laminate material to the form; selecting a hinged boot shell based on the size of the person's foot, ankle and calf; using the tri-laminate covered form to press a deformable material into a mold shaped to match a portion of the hinged boot shell; removing the insole consisting of the partially covered tri-laminate from the mold and removing the from the insole; and inserting the insole into the selected boot shell.

It is contemplated that an instance of an embodiment of the present invention may be characterized as a method of producing a boot having an insole customized to fit a particular foot of a particular person, the method comprising: (a) producing a form that at least partially duplicates the bottom and sides of the foot; (b) selecting a boot shell assembly having a cavity sized and dimensioned to receive the foot and the customized insole; (c) obtaining a boot mold that duplicates a portion of the bottom and sides of the cavity; and (d) producing the customized insole using the produced form to shape a foot receiving cavity of the insole and using the boot mold to shape the bottom and sides of the insole.

In the preceding or other instances, the method may further comprise one or more of the following: (a) pre-fabricating a plurality of shell assemblies where each shell assembly is one of a limited number of pre-selected sizes, and selecting a boot shell assembly comprises selecting one of the plurality of pre-fabricated shell assemblies; (b) pre-fabricating a plurality of ancillary assemblies to be used with the pre-fabricated shell assemblies wherein such ancillary assemblies comprise one or more of the following: a fastening assembly, a sole assembly, and a weight distribution assembly; (c) using some of the pre-fabricated ancillary assemblies to produce a customized boot by combining a pre-fabricated shell assembly with at least one pre-fabricated ancillary assembly and the customized insole.

In the preceding or other instances, producing a form that at least partially duplicates the bottom and sides of the foot may comprise one or more of the following: (a) having the person use the foot to step on a layer of material to create a form mold foot cavity in the material that duplicates the bottom and sides of the foot; (b) filling the form mold foot cavity with a fill material that will solidify into a form that retains the shape of the form mold foot cavity; (c) removing the form from the form mold foot cavity; (d) modifying the form such that it does not duplicate the bottom and sides of the toes of the foot as well as it did when it was first removed from the form mold foot cavity; and (e) filling indentations in the form and/or removing portions of the form.

In the preceding or other instances, producing the customized insole may comprise one or more of the following: (a) molding a first material to the form to create a lined form; (b) using the lined form to press a layer of a second material into the boot mold;. In some such instances the first material may be a tri-laminate material comprising a first closed cell, polyethylene foam layer; a frothed, open cell urethane sheet layer; and a second closed cell, polyethylene foam layer having a higher density that the first closed cell, polyethylene foam layer; and the second material may be a foamed plastic.

What is claimed is:

1. A method of producing a boot having an insole customized to fit a particular foot of a particular person comprising:
producing a form that at least partially duplicates the bottom and sides of the person's foot;
selecting a boot shell assembly having a cavity sized and dimensioned to receive the person's foot;
obtaining a boot mold that duplicates a portion of a bottom and sides of the cavity; and
producing a customized insole using the produced form to shape a foot receiving cavity of the insole including molding a first material to the produced form to create an upper lined material to provide a conforming surface for the person's foot and using the upper lined material to press a second material into the boot mold to form a complementary bottom layer having a shape to conform with an interior surface of the boot shell assembly to form a bottom surface and sides of the customized inside.

2. The method of claim 1 further comprising pre-fabricating a plurality of shell assemblies where each shell assembly is one of a limited number of pre-selected sizes, and selecting a boot shell assembly comprises selecting one of the plurality of pre-fabricated shell assemblies.

3. The method of claim 2 further comprising pre-fabricating a plurality of ancillary assemblies to be used with the pre-fabricated shell assemblies wherein such ancillary assemblies comprise at least one of each of the following: a fastening assembly, a sole assembly, and a weight distribution assembly.

4. The method of claim 2 further comprising pre-fabricating a plurality of ancillary assemblies to be used with the pre-fabricated shell assemblies wherein such ancillary assemblies comprise one or more of the following: a fastening assembly, a sole assembly, and a weight distribution assembly.

5. The method of claim 4 further comprising using some of the pre-fabricated ancillary assemblies to produce a customized boot by combining a pre-fabricated shell assembly with at least one pre-fabricated ancillary assembly and the customized insole.

6. The method of claim 1 wherein producing a form that at least partially duplicates the bottom and sides of the foot comprises:
having the person use the foot to step on a layer of material to create a form mold foot cavity in the material that duplicates the bottom and sides of the foot;
filling the form mold foot cavity with a fill material that will solidify into a form that retains the shape of the form mold foot cavity; and
removing the form from the form mold foot cavity.

7. The method of claim 6 further comprising modifying the form such that it does not duplicate the bottom and sides of the toes of the foot as well as it did when it was first removed from the form mold foot cavity.

8. The method of claim 7 wherein modifying the form comprises filling indentations in the form and/or removing portions of the form.

9. The method of claim 1 wherein:
the first material is a tri-laminate material comprising
a first closed cell, polyethylene foam layer;
a frothed, open cell urethane sheet layer; and
a second closed cell, polyethylene foam layer having a higher density that the first closed cell, polyethylene foam layer; and
the second material is a foamed plastic.

10. A method of producing a diabetic boot customized to a foot, comprising the steps of:
forming a mold of the person's foot;
using the mold to cast a form having a surface matching the bottom and sides of the person's foot;
modifying the form to eliminate toe specific indentations;
molding a tri-laminate material to the form;
selecting a boot shell, from a plurality of different size boot shells based on the size of the person's foot, ankle and calf;
using the tri-laminate material to press and enable a setting of a deformable material into a mold shaped to match a portion of the boot shell to form an insole with an upper surface of the tri-laminate material and a lower surface of the deformable material set to match the portion of the boot shell;
removing the insole of the tri-laminate material and set deformable material from the mold; and
inserting the insole into the selected boot shell.

11. The method of claim 10 wherein the insole includes tri-laminate material having a medium density closed cell polyethylene layer, a urethane layer, and a higher density closed cell polyethylene layer forming a foot receiving liner cavity, and a layer of polyethylene foam forming the lower external surface of the insole.

12. The method of claim 11 further modifying the insole to provide one or more recesses to accommodate one or more sores on the person's foot.

13. The method of claim 11 further providing a flexible first front weight distribution liner and a flexible second rear weight distribution liner of respective size for conforming to the person's foot and removably adhering the respective first and second liners to the boot shell.

14. The method of claim 13 wherein the selection of the boot shells is from a plurality of hinged boot shells comprising an upper shell hinged adjacent a toe portion to a lower shell.

15. The method of claim 14 further comprising providing a releasable fastening assembly to fasten the upper shell relative to the lower shell to encompass the person's foot.

16. The method of claim 15 further comprising fitting a sole assembly of a rocker member and a tread member to a bottom surface of the lower shell for contact with a support surface.

17. The method of claim 14 further comprising positioning a first viscoelastic pad above the insole and between the first removable liner and the lower shell, and a second viscoelastic pad extending along a length of the second removable liner and positioned between the second removable liner and the upper shell.

18. The method of claim 17 wherein the first viscoelastic pad is coupled to the first removable liner by a hook-and-loop fastener, the second viscoelastic pad extends into pockets positioned at the ends of the second removable liner, the first liner is coupled to the bottom shell by a hook-and-loop fastener positioned near an upper end of the lower shell, the first removable liner has a lower end sandwiched between the insole and the lower shell, and the second removable liner is coupled to the upper shell by hook-and-loop fasteners coupled to the pockets holding the second viscoelastic pad.

19. The method of claim 13 wherein each liner includes a cloth exterior enclosing an open-cell polyester or polyether foam and has a thickness of less than 0.25 inches.

20. A method of producing a boot for a foot having an insole customized to fit a user's foot, comprising the steps of:
producing a form that at least partially duplicates the bottom and sides of the user's foot;
selecting a boot shell assembly, from a plurality of boot shell assemblies, having a cavity, sized and dimensioned, to receive both the user's foot and a customized insole;
obtaining a boot mold that duplicates a portion of the bottom and sides of the cavity of the boot shell assembly;
producing the customized insole using the produced form to shape a foot receiving cavity of the insole and using the boot mold to shape the bottom and sides of the insole, wherein the customized insole comprises a tri-laminate material having a medium density closed cell polyethylene layer, a urethane layer, and a higher density closed cell polyethylene layer forming an upper surface cavity, and a layer of polyethylene foam forming the lower external surface of the insole; and
assembling the customized insole in the selected boot shell assembly.

21. The method of claim 20 wherein plurality of boot shell assemblies each include a lower shell and an upper shell that overlaps the lower shell.

22. The method of claim 21 further including fastening the upper shell and lower shell about the user's foot with a pair of straps.

23. The method of claim 22 wherein the upper shell and lower shell are fastened by positioning each strap to overlay the upper shell at or above a bend in the shell where the shell transitions between an ankle and/or calf segment and a foot segment.

24. The method of claim 20 wherein the customized insole is provided with a foot receiving cavity having edges shaped to substantially conform to a perimeter of the user's foot and a bottom shaped to substantially conform to the bottom of the user's foot.

25. The method of claim 22 wherein the foot receiving cavity includes one or more recesses positioned to be adjacent to one or more sores or ulcers on the user's foot.

26. The method of claim 25 wherein the insole has an external surface comprising the bottom and sides of the insole where the surface is sized and dimensioned to match the shape of the bottom and lower portions of the sides of the lower shell.

* * * * *